US010251684B2

(12) United States Patent
Nardini et al.

(10) Patent No.: US 10,251,684 B2
(45) Date of Patent: Apr. 9, 2019

(54) MONOFIX NAIL

(75) Inventors: Reto Nardini, Langendorf (CH); Alfred Niederberger, Langendorf (CH); Azagen Mootien, Langendorf (CH); Frank Wilson, West Chester, PA (US)

(73) Assignee: Depuy Synthes Products, Inc., Raynham, MA (US)

( * ) Notice: Subject to any disclaimer, the term of this patent is extended or adjusted under 35 U.S.C. 154(b) by 1493 days.

(21) Appl. No.: 13/523,227

(22) Filed: Jun. 14, 2012

(65) Prior Publication Data

US 2013/0150851 A1      Jun. 13, 2013

Related U.S. Application Data

(60) Provisional application No. 61/500,284, filed on Jun. 23, 2011, provisional application No. 61/531,417, filed on Sep. 6, 2011.

(51) Int. Cl.
*A61B 17/72* (2006.01)

(52) U.S. Cl.
CPC ...... *A61B 17/7233* (2013.01); *A61B 17/7266* (2013.01)

(58) Field of Classification Search
CPC . A61B 17/72; A61B 17/7233; A61B 17/7283; A61B 17/7266; A61B 17/7225; A61B 17/7216; A61B 17/744; A61B 17/725; A61B 17/746; A61B 17/742
USPC .................................................. 606/62–68
See application file for complete search history.

(56) References Cited

U.S. PATENT DOCUMENTS

| 2,327,434 | A | | 8/1943 | Johnston | |
|---|---|---|---|---|---|
| 2,396,276 | A | | 3/1946 | Lang | |
| 4,653,487 | A | * | 3/1987 | Maale | 606/62 |
| 4,781,181 | A | * | 11/1988 | Tanguy | 606/64 |
| 5,569,249 | A | * | 10/1996 | James et al. | 606/62 |
| 5,810,820 | A | * | 9/1998 | Santori et al. | 606/63 |
| 5,814,047 | A | | 9/1998 | Emilio et al. | |
| 5,976,139 | A | * | 11/1999 | Bramlet | 606/66 |
| 2003/0187447 | A1 | * | 10/2003 | Ferrante et al. | 606/73 |

FOREIGN PATENT DOCUMENTS

| EP | 0517435 | | 12/1992 | |
|---|---|---|---|---|
| EP | 0922437 | | 6/1999 | |
| EP | 0922437 | A1 * | 6/1999 | ............ A61B 17/72 |
| FR | 2668920 | | 5/1992 | |
| WO | 1995/031942 | | 11/1995 | |

(Continued)

*Primary Examiner* — Ellen C Hammond
*Assistant Examiner* — Tessa Matthews
(74) *Attorney, Agent, or Firm* — Fay Kaplun & Marcin, LLP (57) ABSTRACT

An intramedullary device includes an intramedullary nail extending along a longitudinal axis from a proximal end to a distal end, the nail including a channel extending longitudinally therethrough and an opening extending laterally through a wall thereof proximate the distal end, the channel including a ramped surface along a distal portion thereof opposite the opening. The device further includes a wire extending along a longitudinal axis from a proximal end to a distal end, the wire sized and shaped to be inserted into the channel of the nail such that the distal end engages the ramped surface to extend through the opening.

23 Claims, 7 Drawing Sheets

(56) References Cited

FOREIGN PATENT DOCUMENTS

| | | |
|---|---|---|
| WO | 1998/003124 | 1/1998 |
| WO | 2002/011632 | 2/2002 |
| WO | 2002/071961 | 9/2002 |
| WO | 2004/049963 | 6/2004 |
| WO | 2007/125497 | 11/2007 |

\* cited by examiner

MONOFIX NAIL

PRIORITY CLAIM

The present invention claims priority to U.S. Provisional Application Ser. No. 61/500,284 filed on Jun. 23, 2011 and entitled "Monofix Nail" and U.S. Provisional Application Ser. No. 61/531,417 filed on Sep. 6, 2011 and entitled "Monofix Nail," the entire disclosures of which are incorporated herein by reference.

BACKGROUND

Intramedullary nails are inserted into medullary canals of long bones to fix fractures thereof. Once inserted into a medullary canal, an intramedullary nail is generally fixed therein by inserting one or more bone fixation elements through locking holes extending transversely through the nail. The curvature of a medullary canal often deviates from the initial curvature along which the nail extends so that the nail is deformed during insertion. This deformation moves the transverse locking holes away from their expected position making it difficult to drill the holes required to insert the locking screws therein.

SUMMARY OF THE INVENTION

The present invention relates to an intramedullary device, which includes an intramedullary nail extending along a longitudinal axis from a proximal end to a distal end, the nail including a channel extending longitudinally therethrough and an opening extending laterally through a wall thereof proximate the distal end, the channel including a ramped surface along a distal portion thereof opposite the opening, and a wire extending along a longitudinal axis from a proximal end to a distal end, the wire sized and shaped to be inserted into the channel of the nail such that the distal end engages the ramped surface to extend through the opening.

DETAILED DESCRIPTION

The present invention may be further understood with reference to the following description and the appended drawings, wherein like elements are referred to with the same reference numerals. The present invention relates to bone treatment devices and, in particular, relates to an intramedullary device. Exemplary embodiments of the present invention describe an intramedullary device including an intramedullary nail and a fixation wire inserted into a channel of the nail such that a distal end of the wire extends out of a distal hole of the nail. Thus, the intramedullary nail may be fixed to the bone from within the nail via the wire such that additional incisions and bone drilling are not required. It should be noted that the terms "proximal" and "distal," as used herein refer to a direction toward (proximal) and away from (distal) a surgeon or other user of the device.

As shown in FIGS. 1-9, an intramedullary device 100 comprises an intramedullary nail 102 and a fixation wire 104, which is passed through the intramedullary nail 102 to a distal hole 106 including a ramped surface angled to engage a wire and pass it out of the nail 102 as will be described in more detail below to fix the nail 102 at a desired location within a bone. The intramedullary nail 102 includes a channel 108 longitudinally therethrough such that the distal hole 106 extends through a transverse wall 110 of the nail 102 from an interior of the nail 102 defined by the channel 108 to an exterior of the nail 102. A distal surface of the distal hole 106 is ramped as described below to engage the distal end of the wire 104 and guide the wire 104 away from the longitudinal axis of the nail 102 out of the distal hole 106. Thus, the fixation wire 104 passes through the channel 108 with a distal end 112 of the wire 104 exiting the nail 102 via the distal hole 106 angled relative to a longitudinal axis of the nail 102 to penetrate bone adjacent to the transverse surface of the nail 102 fixing the nail 102 within the bone. The wire 104 may include a self tapping end so that the nail 102 may be fixed to the bone from within the nail 102 (i.e., without requiring the predrilling of a hole to receive the wire). Thus, a location of the distal hole 106 after insertion of the nail 102 into the bone does not need to be identified and drilled from outside the body.

A shown in FIGS. 1-4, the intramedullary nail 102 extends along a longitudinal axis from a proximal end 114 to a distal end 116 and includes the channel 108 extending therethrough along the longitudinal axis. The distal hole 106 extends transversely through the wall 110 proximate the distal end 116. The channel 108 includes a ramped surface 118 extending along a portion thereof corresponding to a position of the distal hole 106 such that when the fixation wire 104 passes through the channel 108, the distal end 112 of the wire 104 slides along the ramped surface 118 and is guided through the distal hole 106 to an exterior of the nail 102. The distal hole 106 may be elongated along a length of the nail 102 such that the distal end 112 of the wire 104 may easily pass transversely therethrough while also providing sufficient access for manufacturing (e.g., milling) the ramped surface 118. A distal portion 120 of the channel 108 distal of the ramped surface 118 and the distal hole 106 may have a smaller diameter than a proximal portion 122 of the channel 108 proximal of the ramped surface 118 such that the channel 108 may still accommodate a guide wire therethrough. In addition, a portion 142 of the channel 108 extending about the distal hole 106 may also have a slightly larger cross-section than the proximal portion 122 such that the distal end 112 of the wire 104 does not come into contact therewith as it is being driven (e.g., rotated) into the bone. In other words, a portion of the wall 110 surrounding the distal hole 106 may have a smaller thickness that a remaining portion of the wall 110.

The channel 108 may also include a shoulder 154 distally of a proximal opening 152 thereof. The shoulder 154 extends radially inward such that a diameter of the channel 108 proximal of the shoulder 154 is larger than a diameter distal of the shoulder 154. Thus, as will be described in further detail below, the shoulder 154 may engage a portion of the wire 104 and/or a portion of a driving tool to prevent the wire 104 from being inserted any further distally through the channel 108.

The nail 102 according to this embodiment of the invention includes a proximal locking hole 124 extending through the wall 110 proximate the proximal end 114 of the nail 102. The proximal locking hole 124 extends through the wall 110 along a central axis angled with respect to the longitudinal axis of the nail 102. The proximal locking hole 124 opens to a chamber formed at a proximal end of the nail 102 so that it is accessible from a proximal opening 152 of the channel 108 at the proximal end 114 so that a bone fixation element 126 may be through the proximal locking hole 124 via the proximal opening 152 so that a shaft 128 of the bone fixation element 126 extends into the bone surrounding the channel 108. Thus, the shaft 128 of the bone fixation element 126 extends out of the nail 102 into the bone along the central axis of the proximal locking hole 124, at an angle relative to the longitudinal axis of the nail 102. An interior surface of the proximal locking hole 124 may be threaded to engage a threading of a head portion of the bone fixation element 126 to lock the bone fixation element 126 in a desired position in the nail 102 as would be understood by those skilled in the art.

The nail 102 may additionally include conventional locking holes extending transversely through the nail 102 to receive additional bone fixation elements therethrough. For example, the nail 102 may include a conventional locking hole 130 extending transversely through a proximal or distal portion of the nail 102. The conventional locking holes 130 may be located using conventional aiming arms known in the art so that a corresponding hole may be pre-drilled into the bone for the insertion of additional bone fixation elements therethrough, as would be understood by those of skill in the art. It will also be understood by those of skill in the art, that a hole may also be pre-drilled into the bone to correspond to the proximal locking hole 124. Alternatively, the bone fixation element 126 may include a self-drilling tip.

Figure 9A:
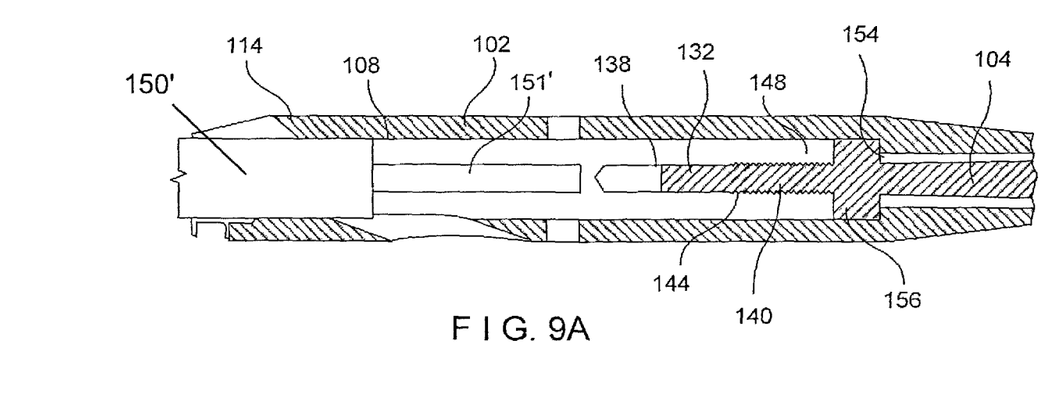
FIG. 9A shows a longitudinal cross-sectional view of the proximal portion of an intramedullary device including an alternate embodiment of an end cap.
Figure 9B:
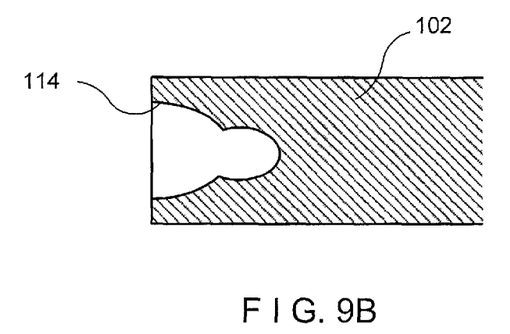
FIG. 9B shows a perspective view of a first alternate embodiment of the proximal portion of an intramedullary device.
Figure 9C:
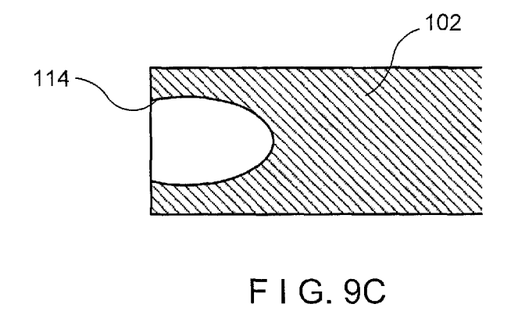
FIG. 9C shows a perspective view of a first alternate embodiment of the proximal portion of an intramedullary device.
Figure 9D:
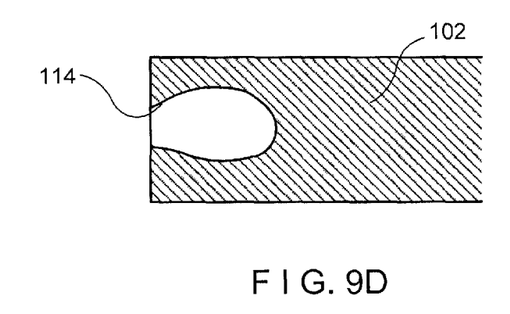
FIG. 9D shows a perspective view of a first alternate embodiment of the proximal portion of an intramedullary device.

The intramedullary device 100 may further comprise an end cap 150 couplable to the proximal end 114 of the intramedullary nail 102 to close the proximal opening 152 of the channel 108. The end cap 150 may be received within the proximal opening 152 and threadedly engaged or otherwise locked therein. The end cap 150 may thus include an engagement structure such as, for example, a hexagonal recess, for engaging an instrument which drives the end cap 150 into the proximal opening 152. In a further embodiment, as shown in FIG. 9A, an end cap 150' may be substantially similar to the end cap 150 but further includes a distally extending portion 151' such that when the end cap 150' is received within the proximal opening 152, the portion 151' prevents the wire 104 from moving proximally relative to the nail 102.

Figure 1:
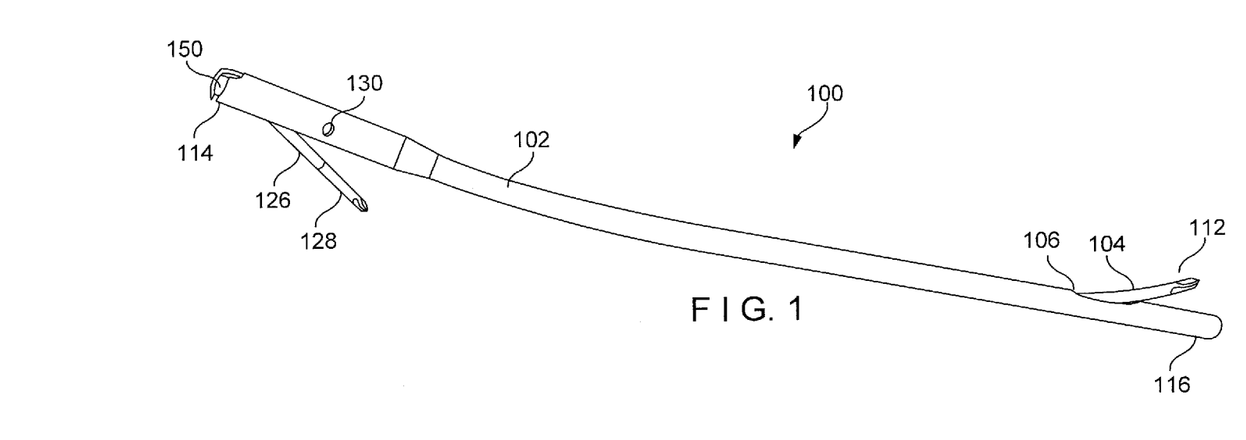
FIG. 1 shows a side view of a device according to an exemplary embodiment of the present invention.
Figure 2:
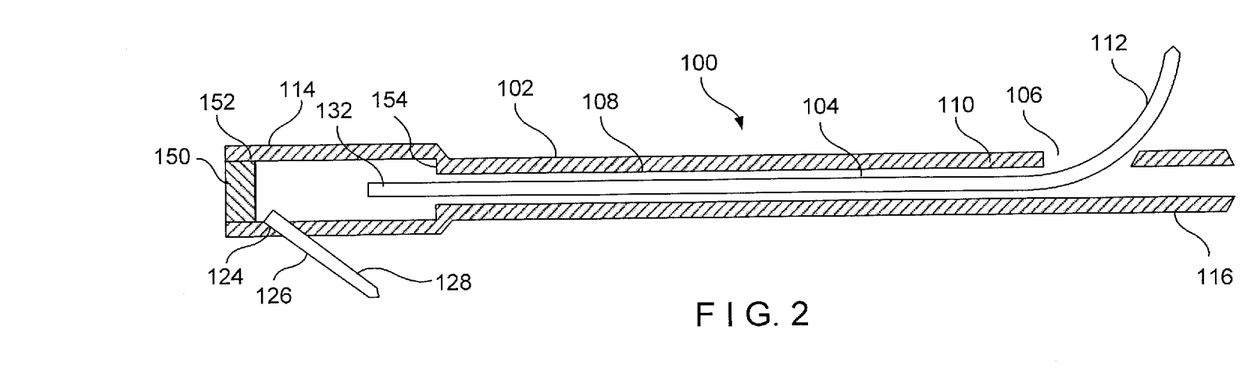
FIG. 2 shows a longitudinal cross-sectional view of the device according to FIG. 1.
Figure 3:
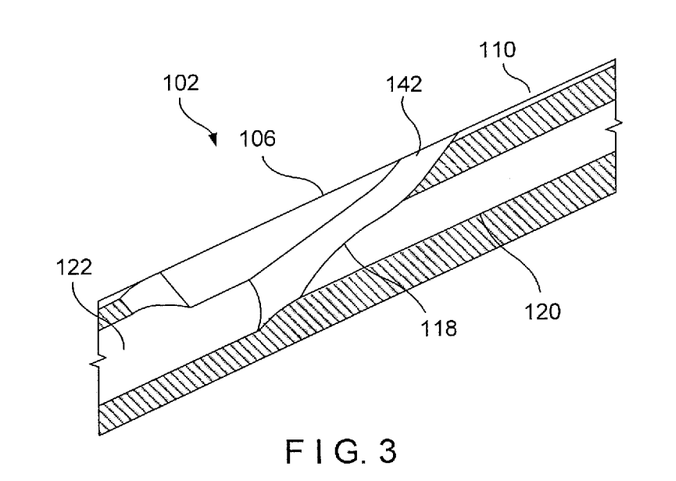
FIG. 3 shows a longitudinal cross-sectional view of a portion of an intramedullary nail of the device according FIG. 1.
Figure 4:
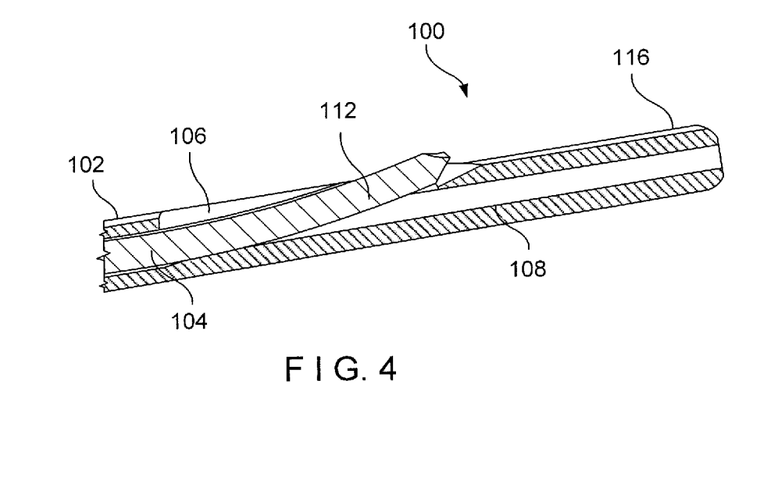
FIG. 4 shows a longitudinal cross-sectional view of a distal portion of the device according to FIG. 1.
Figure 5:
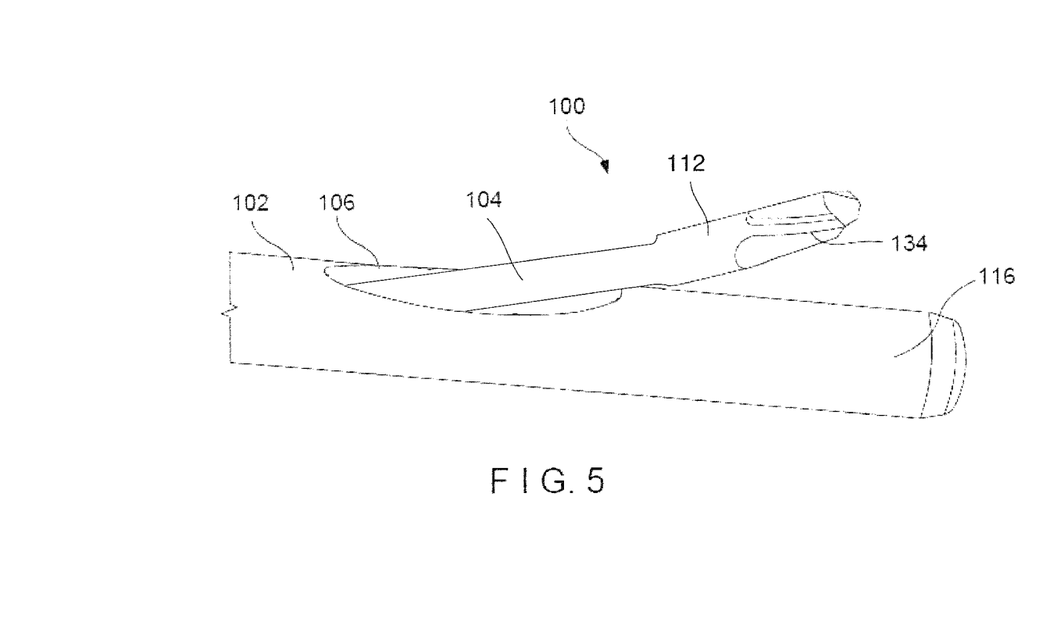
FIG. 5 shows an enlarged perspective view of a distal end of a fixation wire extending out of a distal hole of the intramedullary nail, according to the device of FIG. 1.
Figure 6:
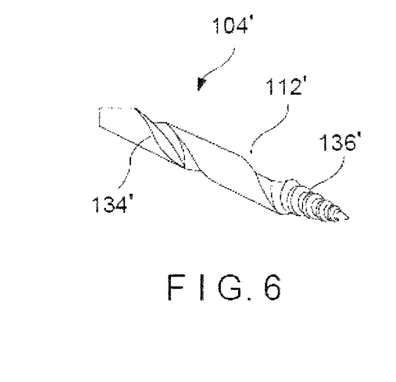
FIG. 6 shows a perspective view of a distal end of a fixation wire according to an alternate embodiment of the present invention.

The wire 104 extends through the opening 152 into the channel 108 and passes therethrough along the longitudinal axis of the nail 102. The ramped portion 118 of the channel 108 is formed on a side of the channel 108 opposite the distal hole 106 and angled toward the distal hole 106 so that, as the distal end 112 engages the ramped portion 118, the distal end of the wire 104 passes into the distal hole 106. As indicated above, the distal end 112 may include a self-drilling tip 134 (shown in FIG. 5) so that as the wire 104 passes out of the nail 102, the self-drilling tip 134 permits the distal end 112 to be inserted into the surrounding bone. A diameter of the distal end 112 of the wire 104 may be larger than a diameter of a remaining length of the wire 104 such that a natural inflection point is formed along the wire 104 at the place where the distal end 112 meets the remaining length of the wire 104. For example, the distal end 112 may have a diameter of approximately 4.0 mm while the remaining length of the wire 104 has a diameter of approximately 3.2 mm. Thus, when the distal end 112 comes into contact with the ramped portion 118, the distal end 112 bends at this inflection point so that it is angled toward the distal hole 106 such that the distal end 112 extends through the hole 106 and into the surrounding bone. In another embodiment, as shown in FIG. 6, a wire 104' has a distal end 112' including a threaded conical tip 136' in addition to a self-drilling portion 134' immediately proximal thereto to provide improved engagement with the bone and increase a fixation stability thereof.

Figure 7A:
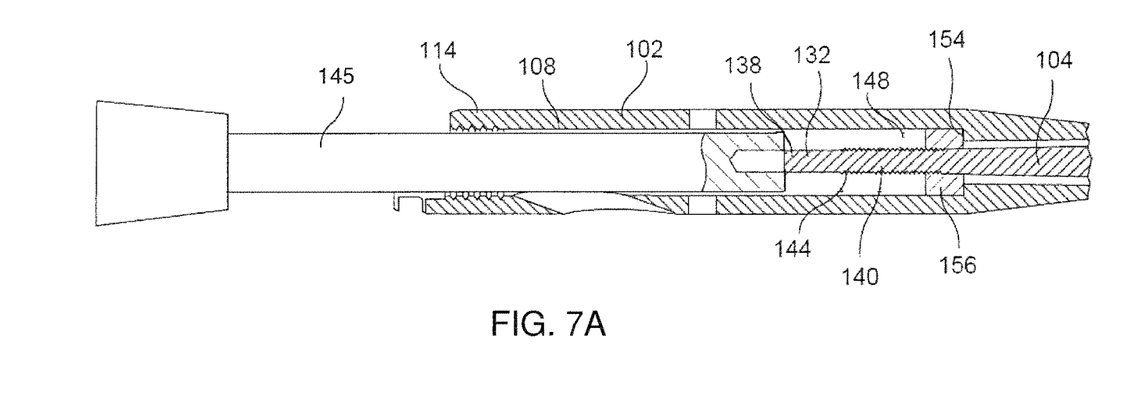
FIG. 7A shows a longitudinal cross-sectional view of a driving tool coupled to the fixation wire according to the device of FIG. 1.
Figure 7B:
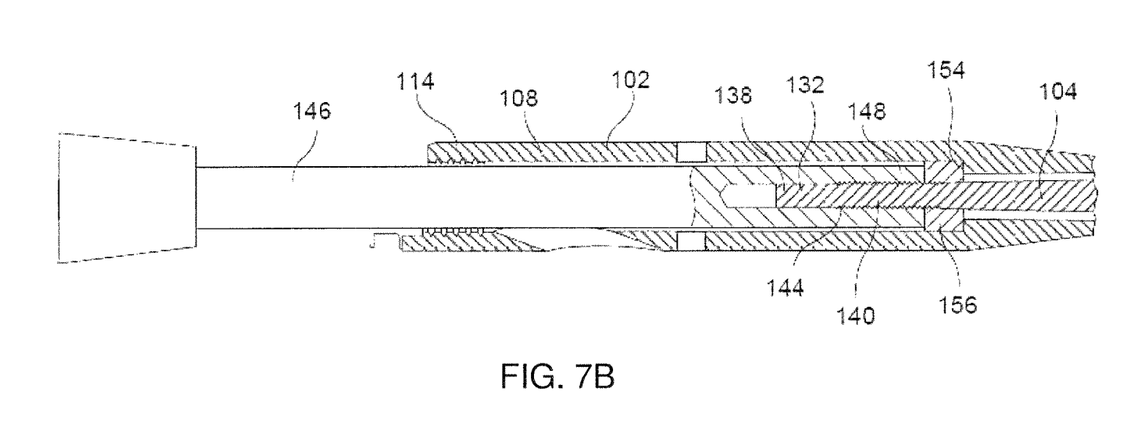
FIG. 7B shows a longitudinal cross-sectional view of a removal tool coupled to the fixation wire according to the device of FIG. 1.

As shown in FIG. 7A, the proximal end 132 of the wire 104 according to this embodiment includes an engagement portion 138 sized and shaped to engage a portion of a driving tool 145 which may be used to rotate the wire 104 to drive the distal end 112 of the wire 104 distally through the distal hole 106 and into bone. The engagement portion 138 may be, for example, hexagonal to engage a corresponding hexagonal portion of the driving tool 145 or may have any other shape which will non-rotatably mate with an end of the driving tool, as would be understood by those skilled in the art. As shown in FIG. 7B, the proximal end 132 may also include a threaded portion 140 distally of the engagement portion 138 to engage a removal tool 146. The threaded portion 140 includes threading along an outer surface of the wire 102 configured to engage corresponding threading 144 along a portion of the removal tool 146. The removal tool 146 may be, for example, a longitudinal element including threads 144 along an interior surface of a distal end 148 thereof for coupling to the threaded portion 138 of the wire 104 such that, once the removal tool 146 and the wire 104 are coupled, the removal tool 146 may be both rotated to rotate the wire 104 and pulled proximally to draw the wire 104 proximally. If the self-drilling tip 126 of the wire 104 extends along the distal end 112 in a right side orientation (i.e., requiring a right side rotation to be drilled into the bone) the threads along the threaded portion 140 will be in a left orientation such that upon threadedly engaging the removal tool 146 to the threaded portion 140, the user may continue to rotate the removal tool 146 to the left side to disengage the distal end 112 from the bone. Once the distal end 112 is disengaged from bone, the user may pull the removal tool 146 proximally to draw the wire 104 out of the channel 108.

Figure 8:
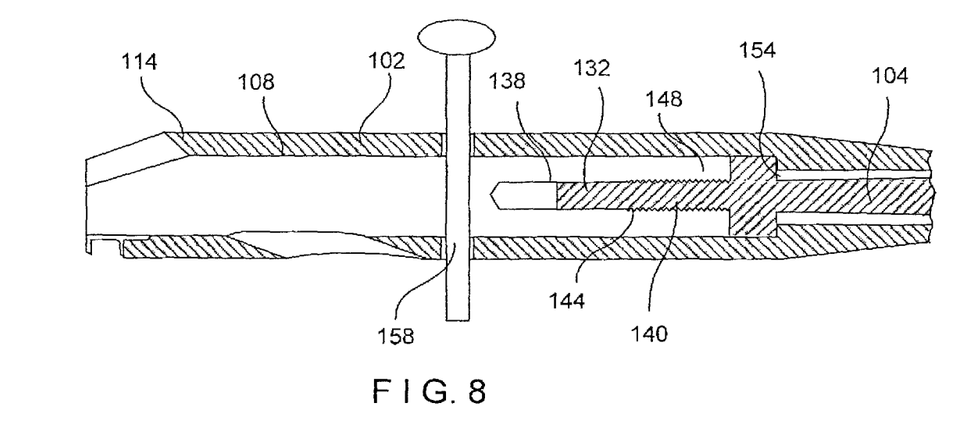
FIG. 8 shows a longitudinal cross-sectional view of a proximal portion of the intramedullary device of FIG. 1.

In one exemplary embodiment, a portion of a driving tool engaging the engagement portion 138 may be sized and shaped to engage the shoulder 154 of the channel 108 such that when the driving tool abuts the shoulder 154, the driving tool and thereby the wire 104 is prevented from being moved any further distally relative to the nail 102. In another embodiment, as shown in FIGS. 8 and 9A, the wire 104 may include a stop 156 proximal of the engagement portion 138 and the threaded portion 140, which extends radially outward and is sized and shaped to engage the shoulder 154. Thus, when the stop 156 abuts the shoulder 154, the wire 104 is prevented from moving any further distally relative to the nail 102.

Figure 10:
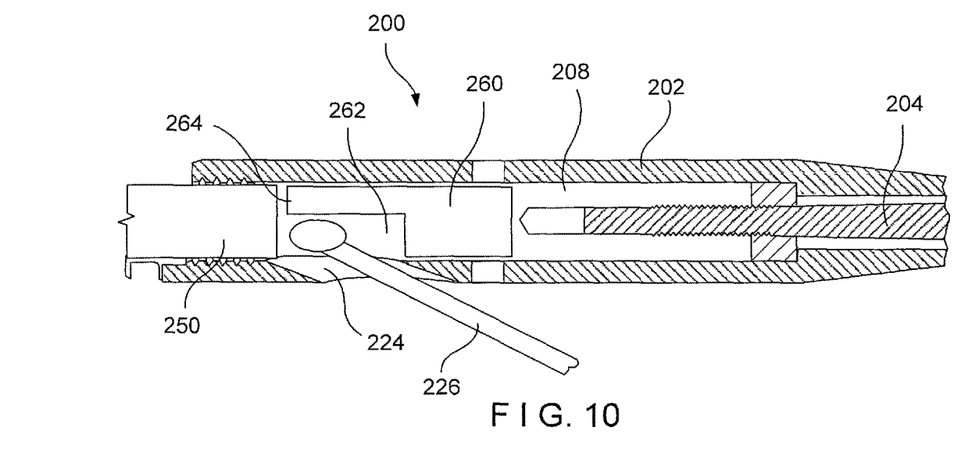
FIG. 10 shows a longitudinal cross-sectional view of a proximal portion of an intramedullary device according to a further exemplary embodiment of the present invention.

As shown in FIG. 10, an intramedullary device 200 according to a further embodiment of the present invention is substantially similar to the intramedullary device 100, but further comprises an insert 260 which may be inserted into a channel 208 of an intramedullary nail 202 to prevent a wire 204 passed therethrough from migrating proximally once it has been inserted into the nail 202 to fix the nail 202 within a bone. The insert 260 may be sized and shaped to engage the channel 208. For example, the insert 260 may threadedly engage the proximal end of the channel 208. The insert 260 may further include a groove 262 extending therealong from a proximal end 264 thereof sized and shaped to permit a bone fixation element 226 to be inserted through a proximal locking hole 224 of the nail 202 after insertion of the insert 260 in the channel 208. Upon positioning of the wire 204 within the channel 208, as desired, the insert 260 is inserted into the channel 208 proximally of the wire and positioned therein such that the groove 262 is aligned with the proximal locking hole 224 of the nail 202. The insert 260 prevents the wire 204 from moving proximally relative to the nail 202 while also permitting the bone fixation element 226 to be inserted through the proximal locking hole 224. An end cap 250, which may be substantially similar to the end cap 150, may then engage the proximal end of the channel 208 to prevent bone ingrowth within the channel 208.

Figure 11:
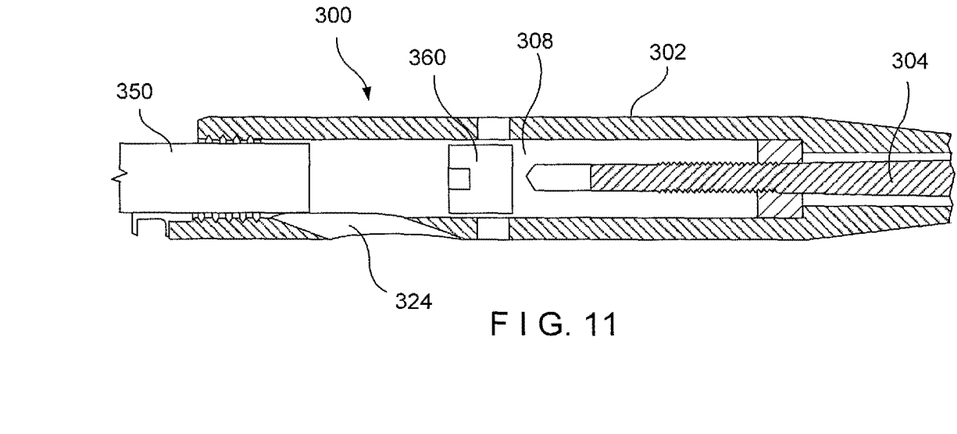
FIG. 11 shows a longitudinal cross-sectional view of a proximal portion of an intramedullary device according to another exemplary embodiment of the present invention.

As shown in FIG. 11, an intramedullary device 300 according to another embodiment of the present invention is substantially similar to the intramedullary device 200 described above except that the device 300 comprises an insert 360 which does not include a groove. Rather, a length of the insert 360 is selected so that, once inserted into a channel 308 of an intramedullary nail 302, it does not interfere with a proximal locking hole 324 thereof. Thus, the insert 360 may be inserted into the channel 308 proximally of a wire 304 while still permitting a bone fixation element to be inserted through the proximal locking hole 324, if desired. An end cap 350, which may be substantially similar to the end caps 150, 250, may then be inserted into the proximal end of the channel 308 to prevent bone ingrowth within the channel 308.

According to a surgical technique using the intramedullary device 100, the intramedullary nail 102 is inserted into a medullary canal of a bone along a guide wire inserted into the medullary canal of the bone and received within the channel 108 as would be understood by those skilled in the art. Once the intramedullary nail 102 has been positioned within the medullary canal as desired, the guide wire may be removed and the nail 102 is fixed within the bone by inserting the wire 104 into the channel 108. As described above, the wire 104 is inserted distally into the channel 108 until the distal end 112 comes into contact with the ramped surface 118 and is directed laterally out of the distal hole 106. As the distal end 112 passes through the distal hole 106 and comes into contact with the bone, the wire 104 may be rotated, for example, using a driving tool engaging the engagement portion 138 of the wire 104. As described above, the wire 104 is inserted into the channel 108 until a portion of the driving tool or the stop 156 abuts the shoulder 154, preventing the wire 104 from being moved any further distally relative to the nail 102. Thus, the distal end 112 is prevented from penetrating the cortical wall. The self drilling tip 134 of the wire 104 permits the distal end 112 to extend into the bone, thereby fixing the nail 102 and the wire 104 relative thereto. It will be understood by those of skill in the wire 104' may be used in a substantially similar manner as the wire 104.

Once the distal end 112 has been inserted into the bone, the bone fixation element 126 is inserted through the proximal opening 152 into the proximal locking hole 124 to extend out of the nail 102 and engage the surrounding bone, fixing the proximal end 114 of the nail 102 in a desired position relative to the bone. As described above, the bone fixation element 126 is inserted into the proximal hole 124 along the central axis thereof such that the shaft 128 of the bone fixation element 126 extends at an angle relative to the longitudinal axis of the nail 102. Where there are additional locking holes along the nail 102, additional bone fixation elements may be guided and inserted therethrough using a conventional aiming arm attached to the proximal end 114 of the nail 102. Once the intramedullary nail 102 has been fixed within the bone, the end cap 150 may be coupled to the proximal end 114 of the nail 102. The end cap 150 may be received within the proximal opening 152 and rotated relative thereto to threadedly engage the proximal end 114 and close the proximal opening 152, thus preventing bone ingrowth therein. In addition, as shown in FIG. 8, a bone fixation element 158 may be inserted through a proximal locking hole of the nail 102 positioned proximally of the proximal end 132 of the wire 104 to prevent the wire 104 from migrating proximally relative to the nail 102 once inserted to the desired position relative thereto. In another embodiment, as shown in FIG. 9, the end cap 150' may be received within the proximal opening 152 such that the portion 151' extends distally into the channel 108 proximally of the proximal end 132 of the wire 104. The portion 151' thus prevents the wire 104 from migrating proximally within the channel 108 once inserted therein in the desired position. The end cap 150' may, for example, be utilized when only distal locking is required.

If, at any point, subsequent to the fixation the patient requires removal of the intramedullary nail 102, the end cap 150 may be disengaged from the nail 102 and the bone fixation element 126 and/or the bone fixation element 158 removed from the proximal hole 124. The distal end 148 of the removal tool 146 may be inserted into the channel 108 to engage the threaded portion 140 of the wire 104. Once the removal tool 146 and the wire 104 have been coupled, the removal tool 146 may be rotated, in an opposite direction required for driving the wire 104, to disengage the distal end 112 from the bone. The removal tool 146 may then be drawn proximally relative to the nail 102 to pull the wire 104 out of the channel 108 so that the nail 102 may be removed from the bone. It will be understood by those of skill in the art, however, that the distal end 112 of the wire 104 is only required to be drawn within the channel 108 to permit the intramedullary device 100 to be removed from the bone. A diameter of the distal end 112 is smaller than a diameter of the channel 108 such that distal end 112 does not contact the channel 108 as it is drawn therein facilitating this withdrawal.

The intramedullay device 200 may be used in a manner substantially similarly to the device 100, as described above. However, prior to insertion of the bone fixation element 226 through the proximal locking hole 224 and after insertion of the wire 204 in the desired position, the insert 260 is inserted into the channel 208 proximally of the wire 204 to prevent the wire 204 from moving proximally relative to the nail 202. The insert 260 is positioned such that the groove 262 is aligned with the proximal locking hole 224 to permit the bone fixation element 226 to be inserted therethrough. Upon insertion of the bone fixation element 226, the end cap 250 may be coupled to the proximal end of the channel 208. The intramedullary device 300 may be utilized in a substantially similar manner to the intramedullary device 200, but does not require the insert 360 to be positioned in any particular orientation, as a length thereof is particularly selected such that the insert 360 does not interfere with the proximal locking hole 324.

It will be apparent to those of skill in the art that various modifications and variations can be made in the structure and the methodology of the present invention, without departing from the spirit or scope of the invention. For example, any number of different distal holes and corresponding ramped surfaces may be provided (limited by the space in the channel 108) to accommodate multiple wires 104 and, similarly, a plurality of proximal holes 124 may be included separated from one another circumferentially about the longitudinal axis and/or along the longitudinal axis as desired to accommodate a plurality of bone fixation elements 126. Thus, it is intended that the present invention cover the modifications and variations of the invention provided that they come within the scope of the appended claims and their equivalents.

What is claimed is:

1. An intramedullary device, comprising:
   an intramedullary nail extending along a longitudinal axis from a proximal end to a distal end, the nail including a channel extending longitudinally therethrough and an opening extending laterally through a wall thereof proximate the distal end, the channel including a ramped surface along a distal portion thereof opposite the opening; and
   a wire extending along a longitudinal axis from a proximal end to a distal end, the wire sized and shaped to be inserted into the channel of the nail such that the distal end engages the ramped surface to extend through the opening, wherein the wire includes a stop extending radially outward therefrom to engage a shoulder of the channel, and a diameter of the channel proximal of the shoulder is larger than a diameter of the channel distal of the shoulder.

2. The device according to claim 1, wherein the opening is elongated along a length of the nail.

3. The device according to claim 1, wherein the distal end of the wire has a diameter larger than a diameter of a remaining length of the wire.

4. The device according to claim 1, wherein the distal end of the wire includes a self-drilling tip.

5. The device according to claim 1, wherein the distal end of the wire includes a threaded conical tip.

6. The device according to claim 1, wherein the nail includes a lateral opening extending through a wall thereof proximate the proximal end of the nail, the lateral opening sized and shaped to receive a bone fixation element therethrough along a central axis thereof, the central axis angled with respect to the longitudinal axis.

7. The device according to claim 1, wherein a portion of the channel distal of the ramped surface has a smaller diameter than a remaining portion thereof to accommodate a guide wire therein.

8. The device according to claim 1, wherein the proximal end of the wire includes an engagement portion sized and shaped for attachment to an insertion tool.

9. The device according to claim 1, wherein the proximal end includes a threaded portion configured to be coupled to a removal tool.

10. The device according to claim 1, further comprising an insert sized and shaped for insertion into the channel to prevent the wire from moving proximally relative to the nail.

11. The device according to claim 10, wherein the insert includes a groove extending from a proximal end thereof along a length thereof, the groove being sized and shaped such that when the insert is inserted into the channel in a desired position, a bone fixation element is insertable through a proximal locking hole of the nail via the groove.

12. A system for treating a bone, comprising:
    an intramedullary nail extending along a longitudinal axis from a proximal end to a distal end, the nail including a channel extending longitudinally therethrough and an opening extending laterally through a wall thereof proximate the distal end, the channel including a ramped surface along a distal portion thereof opposite the opening;
    a wire extending along a longitudinal axis from a proximal end to a distal end, the wire sized and shaped to be inserted into the channel of the nail such that the distal end engages the ramped surface to extend through the opening; and
    an insertion tool releasably couplable to the proximal end of the wire to drive the distal end of the wire into bone, wherein the insertion tool includes a stop engaging a shoulder of the channel to indicate a desired position of the wire relative to the nail, and a diameter of the channel proximal of the shoulder is larger than a diameter of the channel distal of the shoulder.

13. The system according to claim 12, further comprising a removal tool releasably couplable to the proximal end of the wire to remove the wire from the bone.

14. The system according to claim 13, wherein a distal end of the removal tool threadedly engages a threaded portion along the proximal end of the wire such that the removal tool rotates the wire in a second direction relative to the nail to disengage the distal portion from bone and pulls the wire proximally relative to the nail to draw the wire out of the channel.

15. The system according to claim 12, further comprising an end cap couplable to the proximal end of the nail.

16. The system according to claim 12, wherein the insertion tool includes a recess at a distal end thereof sized and shaped to engage a correspondingly sized and shaped engagement portion on the proximal end of the wire such that the insertion tool rotates the wire in a first direction relative to the nail to drive the distal end of the wire into bone.

17. The system according to claim 12, wherein the nail includes a lateral opening extending through a wall thereof proximate the proximal end of the nail, the lateral opening sized and shaped to receive a bone fixation element therethrough along a central axis thereof, the central axis angled with respect to the longitudinal axis.

18. An intramedullary device, comprising:
- an intramedullary nail extending along a longitudinal axis from a proximal end to a distal end, the nail including a channel extending longitudinally therethrough and an opening extending laterally through a wall thereof proximate the distal end; and
- a wire extending along a longitudinal axis from a proximal end to a distal end, the wire sized and shaped to be inserted into the channel of the nail such that the distal end extends through the opening, the distal end having a diameter that is larger than a diameter of a remaining length of the wire to form a natural bend in the wire, wherein the wire includes a stop extending radially outward therefrom to engage a shoulder of the channel.

19. The device according to claim 18, wherein the channel includes a ramped surface along a portion thereof opposite the opening such that the distal end of the wire engages the ramped surface to extend through the opening.

20. The device according to claim 18, wherein the opening is elongated along a length of the nail.

21. The device according to claim 18, wherein the distal end of the wire includes a self-drilling tip.

22. The device according to claim 18, wherein the distal end of the wire includes a threaded conical tip.

23. The device according to claim 18, wherein the nail includes a lateral opening extending through a wall thereof proximate the proximal end of the nail, the lateral opening sized and shaped to receive a bone fixation element therethrough along a central axis thereof, the central axis angled with respect to the longitudinal axis.

\* \* \* \* \*